United States Patent [19]
Hansen

[11] Patent Number: 6,071,549
[45] Date of Patent: Jun. 6, 2000

[54] BINDER TREATED FIBROUS WEBS AND PRODUCTS

[75] Inventor: Michael R. Hansen, Seattle, Wash.

[73] Assignee: Weyerhaeuser Company, Federal Way, Wash.

[21] Appl. No.: 09/130,723

[22] Filed: Aug. 6, 1998

Related U.S. Application Data

[60] Division of application No. 08/416,375, Apr. 4, 1995, Pat. No. 5,807,364, which is a continuation-in-part of application No. 07/931,059, Aug. 17, 1992, Pat. No. 5,543,215, and application No. 07/931,277, Aug. 17, 1992, Pat. No. 5,538, 783, and application No. 07/931,279, Aug. 17, 1992, Pat. No. 5,589,256, and application No. 08/107,469, Aug. 17, 1993, Pat. No. 5,672,418, and application No. 08/108,219, Aug. 17, 1993, Pat. No. 5,607,759, and application No. 08/107,467, Aug. 17, 1993, Pat. No. 5,693,411, and application No. 08/108,217, Aug. 17, 1993, Pat. No. 5,547,745, and application No. 08/108,218, Aug. 17, 1993, Pat. No. 5,641,561, and application No. 08/197,483, Feb. 16, 1997, Pat. No. 5,547,541, and application No. 08/193,301, Feb. 7, 1994, Pat. No. 5,609,727, and application No. 08/261,811, Jul. 17, 1994, Pat. No. 5,571,618, and application No. 08/153,819, Nov. 15, 1993, Pat. No. 5,447,977.

[51] Int. Cl.$^7$ .............................. B05D 3/12; B05D 5/04; B05D 1/36
[52] U.S. Cl. ..................... 427/2.31; 427/180; 427/202; 427/337; 427/342; 427/369; 427/394
[58] Field of Search .................................. 427/2.31, 195, 427/389.9, 381, 392, 244, 322, 323, 324, 326, 342, 338, 337, 198, 369, 359, 365, 384, 394, 396, 412

[56] References Cited

U.S. PATENT DOCUMENTS

| | | |
|---|---|---|
| 2,601,597 | 6/1952 | Daniel, Jr. et al. . |
| 2,953,187 | 9/1960 | Francis, Jr. . |
| 3,010,161 | 11/1961 | Duvall . |
| 3,021,242 | 12/1962 | Touey . |
| 3,059,313 | 10/1962 | Harmon . |
| 3,070,095 | 12/1962 | Torr . |
| 3,087,833 | 4/1963 | Drelich . |

(List continued on next page.)

FOREIGN PATENT DOCUMENTS

| | | |
|---|---|---|
| 729513 | 3/1966 | Canada . |
| 806352 | 2/1969 | Canada . |
| 813616 | 5/1969 | Canada . |
| 841940 | 5/1970 | Canada . |

(List continued on next page.)

OTHER PUBLICATIONS

Amosov et al., "Aluminum Hydroxy compounds—binders for dry–process paper," *Izv. VUZ, Lesnoi Zh.*, 6:72–76 (1986).

Blanchard and Reinhart, "Dyeing of Crosslinked Cotton Containing Glycol Additives," *U.S. Dept. of Agriculture*, New Orleans, 24:13–17 (Jan. 1992).

(List continued on next page.)

*Primary Examiner*—Diana Dudash
*Attorney, Agent, or Firm*—Christensen O'Connor Johnson & Kindness PLLC

[57] ABSTRACT

Salts of hydroxy acids include functional groups capable of forming "hybrid" ionic bonds with fibers or particles and another functional group capable of forming a hydrogen bond or "hybrid" ionic bond with the fibers when the binder forms a "hybrid" ionic bond with the particles or a hydrogen, coordinate covalent, or "hybrid" ionic bond with the particles when the binder forms a "hybrid" ionic bond with the fibers. Amino acids are also described as binders capable of forming "hybrid" ionic or ionic bonds between fibers and particles. Salts of bases, such as choline chloride are also described as being useful binders for attaching particles to fibers. The salts of bases form ionic bonds with either the particles or the fibers. Such binding systems provide viable alternatives to existing binding systems.

28 Claims, 2 Drawing Sheets

U.S. PATENT DOCUMENTS

| Number | Date | Name | Ref |
|---|---|---|---|
| 3,327,708 | 6/1967 | Sokolowski . | |
| 3,344,789 | 10/1967 | Arnold et al. . | |
| 3,350,486 | 10/1967 | Knoepfler et al. . | |
| 3,377,302 | 4/1968 | Gugliemelli et al. . | |
| 3,395,201 | 7/1968 | Kalwaites . | |
| 3,409,497 | 11/1968 | Roseland . | |
| 3,425,971 | 2/1969 | Gugliemelli et al. . | |
| 3,494,992 | 2/1970 | Wiegand . | |
| 3,521,638 | 7/1970 | Parrish . | |
| 3,554,788 | 1/1971 | Fechillas . | |
| 3,661,154 | 5/1972 | Torr . | |
| 3,661,632 | 5/1972 | Gagliardi et al. . | |
| 3,669,103 | 6/1972 | Harper et al. . | |
| 3,670,731 | 6/1972 | Harmon . | |
| 3,672,945 | 6/1972 | Taylor . | |
| 3,692,622 | 9/1972 | Dunning . | |
| 3,745,060 | 7/1973 | Jumentier et al. . | |
| 3,758,641 | 9/1973 | Zweigle . | |
| 3,766,922 | 10/1973 | Krusko . | |
| 3,777,758 | 12/1973 | Mesek et al. . | |
| 3,788,936 | 1/1974 | Brock et al. . | |
| 3,804,092 | 4/1974 | Tunc . | |
| 3,808,088 | 4/1974 | Knechtges et al. . | |
| 3,886,941 | 6/1975 | Duane et al. . | |
| 3,888,256 | 6/1975 | Studinger . | |
| 3,888,257 | 6/1975 | Cook et al. . | |
| 3,901,236 | 8/1975 | Assarsson et al. . | |
| 3,903,889 | 9/1975 | Torr . | |
| 3,908,659 | 9/1975 | Wehrmeyer et al. . | |
| 3,923,592 | 12/1975 | George et al. . | |
| 3,949,035 | 4/1976 | Dunning et al. . | |
| 3,978,257 | 8/1976 | Ring . | |
| 3,991,237 | 11/1976 | Topfl et al. . | |
| 4,002,171 | 1/1977 | Taft . | |
| 4,007,083 | 2/1977 | Ring et al. . | |
| 4,009,313 | 2/1977 | Crawford et al. . | |
| 4,035,217 | 7/1977 | Kennette et al. . | |
| 4,055,180 | 10/1977 | Karami . | |
| 4,061,268 | 12/1977 | DeMaster . | |
| 4,062,451 | 12/1977 | Gander . | |
| 4,066,789 | 1/1978 | Mores et al. | 424/365 |
| 4,071,636 | 1/1978 | Nishino et al. . | |
| 4,102,340 | 7/1978 | Mesek et al. . | |
| 4,103,062 | 7/1978 | Aberson et al. . | |
| 4,160,059 | 7/1979 | Samejima . | |
| 4,232,674 | 11/1980 | Melican . | |
| 4,250,660 | 2/1981 | Kitamura et al. . | |
| 4,282,121 | 8/1981 | Goodrich . | |
| 4,289,513 | 9/1981 | Brownhill et al. . | |
| 4,289,536 | 9/1981 | Dereser . | |
| 4,310,593 | 1/1982 | Gross | 427/2.31 |
| 4,324,706 | 4/1982 | Tabe et al. . | |
| 4,332,917 | 6/1982 | Heslinga et al. . | |
| 4,338,417 | 7/1982 | Heslinga et al. . | |
| 4,364,992 | 12/1982 | Ito et al. . | |
| 4,379,194 | 4/1983 | Clarke et al. . | |
| 4,394,172 | 7/1983 | Scheuble et al. . | |
| 4,404,250 | 9/1983 | Clarke . | |
| 4,410,571 | 10/1983 | Korpman . | |
| 4,412,036 | 10/1983 | Pederson et al. . | |
| 4,422,949 | 12/1983 | Ooms | 252/8.8 |
| 4,424,247 | 1/1984 | Erickson . | |
| 4,457,978 | 7/1984 | Wawzonek . | |
| 4,467,012 | 8/1984 | Pederson et al. . | |
| 4,486,501 | 12/1984 | Holbek . | |
| 4,492,729 | 1/1985 | Bannerman et al. . | |
| 4,532,176 | 7/1985 | Briggs et al. . | |
| 4,537,767 | 8/1985 | Rothman et al. . | |
| 4,558,091 | 12/1985 | Hubbard . | |
| 4,582,717 | 4/1986 | von Bittera et al. | 427/2.31 |
| 4,597,930 | 7/1986 | Szal . | |
| 4,629,470 | 12/1986 | Harper, Jr. . | |
| 4,673,402 | 6/1987 | Weisman et al. . | |
| 4,676,784 | 6/1987 | Erdman et al. . | |
| 4,699,808 | 10/1987 | Menard et al. . | |
| 4,722,739 | 2/1988 | Blanchard et al. . | |
| 4,725,500 | 2/1988 | Yanai et al. | 428/365 |
| 4,740,528 | 4/1988 | Garvey et al. | 521/128 |
| 4,758,466 | 7/1988 | Dabi et al. . | |
| 4,772,492 | 9/1988 | Bouchette . | |
| 4,788,080 | 11/1988 | Hojo et al. . | |
| 4,818,599 | 4/1989 | Marcus . | |
| 4,826,880 | 5/1989 | Lesniak et al. . | |
| 4,833,011 | 5/1989 | Horimoto . | |
| 4,842,593 | 6/1989 | Jordan et al. . | |
| 4,874,811 | 10/1989 | Borchers et al. . | |
| 4,883,478 | 11/1989 | Lerailler et al. | 604/360 |
| 4,886,697 | 12/1989 | Perdelwitz, Jr. et al. . | |
| 4,892,769 | 1/1990 | Perdelwitz, Jr. et al. . | |
| 4,902,565 | 2/1990 | Brook . | |
| 5,002,814 | 3/1991 | Knack et al. . | |
| 5,015,245 | 5/1991 | Noda | 604/367 |
| 5,057,166 | 10/1991 | Young, Sr. et al. . | |
| 5,064,689 | 11/1991 | Young, Sr. et al. . | |
| 5,100,672 | 3/1992 | Gueret et al. | 424/449 |
| 5,128,082 | 7/1992 | Makoui . | |
| 5,137,537 | 8/1992 | Herron et al. . | |
| 5,145,906 | 9/1992 | Chambers et al. | 524/732 |
| 5,161,686 | 11/1992 | Weber et al. . | |
| 5,217,445 | 6/1993 | Young et al. . | |
| 5,225,047 | 7/1993 | Graef et al. . | |
| 5,230,959 | 7/1993 | Young, Sr. et al. . | |
| 5,234,720 | 8/1993 | Neal et al. | 427/393.1 |
| 5,252,275 | 10/1993 | Sultze et al. . | |
| 5,252,340 | 10/1993 | Honeycutt . | |
| 5,278,222 | 1/1994 | Stack . | |
| 5,278,256 | 1/1994 | Bellis | 525/450 |
| 5,283,123 | 2/1994 | Carter et al. . | |
| 5,300,054 | 4/1994 | Feist et al. . | |
| 5,300,192 | 4/1994 | Hansen et al. . | |
| 5,308,896 | 5/1994 | Hansen et al. . | |
| 5,312,522 | 5/1994 | Van Phan et al. . | |
| 5,312,642 | 5/1994 | Chesterfield et al. | 427/2.31 |
| 5,352,480 | 10/1994 | Hansen et al. . | |
| 5,362,776 | 11/1994 | Barenberg et al. . | |
| 5,432,000 | 7/1995 | Young, Sr. et al. . | |
| 5,447,977 | 9/1995 | Hansen et al. . | |
| 5,498,478 | 3/1996 | Hansen et al. . | |
| 5,538,732 | 7/1996 | Smith et al. | 424/402 |
| 5,538,783 | 7/1996 | Hansen et al. . | |
| 5,543,215 | 8/1996 | Hansen et al. . | |
| 5,547,541 | 8/1996 | Hansen et al. . | |
| 5,547,745 | 8/1996 | Hansen et al. . | |
| 5,571,618 | 11/1996 | Hansen et al. . | |
| 5,589,256 | 12/1996 | Hansen et al. . | |
| 5,607,759 | 3/1997 | Hansen et al. . | |
| 5,609,727 | 3/1997 | Hansen et al. . | |
| 5,611,885 | 3/1997 | Hansen et al. . | |
| 5,614,570 | 3/1997 | Hansen et al. . | |
| 5,641,561 | 6/1997 | Hansen et al. . | |
| 5,672,418 | 9/1997 | Hansen et al. . | |
| 5,693,411 | 12/1997 | Hansen et al. . | |
| 5,757,408 | 5/1998 | Malhotra | 347/105 |
| 5,776,598 | 7/1998 | Huber et al. | 427/2.31 |
| 5,789,326 | 8/1998 | Hansen et al. . | |
| 5,807,364 | 9/1998 | Hansen . | |

FOREIGN PATENT DOCUMENTS

| | | |
|---|---|---|
| 953 890 | 9/1974 | Canada . |
| 1052156 | 12/1976 | Canada . |
| 0 071 063 A1 | 2/1983 | European Pat. Off. . |
| 0 096 976 A2 | 12/1983 | European Pat. Off. . |

| | | |
|---|---|---|
| 0 122042 A2 | 10/1984 | European Pat. Off. . |
| 0 210 754 A1 | 2/1987 | European Pat. Off. . |
| 0 427 316 A2 | 5/1991 | European Pat. Off. . |
| 0 427 317 A2 | 5/1991 | European Pat. Off. . |
| 0 429 112 A2 | 5/1991 | European Pat. Off. . |
| 0 440 472 A1 | 8/1991 | European Pat. Off. . |
| 0 442 185 A1 | 8/1991 | European Pat. Off. . |
| 0 509 708 A1 | 10/1992 | European Pat. Off. . |
| 1 382 716 | 2/1964 | France . |
| 489 308 | 1/1930 | Germany . |
| 1 079 796 | 6/1962 | Germany . |
| 2 048 721 | 6/1971 | Germany . |
| 29 49 531 A1 | 7/1980 | Germany . |
| 61-28422 | 2/1986 | Japan . |
| 1 217 452 | 12/1969 | United Kingdom . |
| 2 007 998 | 5/1979 | United Kingdom . |
| 2 092 895 | 8/1982 | United Kingdom . |
| 2189127 | 10/1987 | United Kingdom . |
| WO 88/01316 | 2/1988 | WIPO . |
| WO 90/09236 | 8/1990 | WIPO . |
| WO 90/11181 | 10/1990 | WIPO . |
| WO 93/24153 | 12/1993 | WIPO . |
| WO 94/04351 | 3/1994 | WIPO . |
| WO 94/04352 | 3/1994 | WIPO . |
| WO 95/00703 | 1/1995 | WIPO . |

OTHER PUBLICATIONS

Burkholder, "Absorbent Polymers—A New Concept in Fluid Absorption," *The Dow Chemical Company Designed Products Laboratory*, Midland, Michigan, pp. 73–79 (1973).

Byrd, "How bonds develop during web consolidation," *PTI*, pp. 240–243 (Oct. 1986).

Gorbushin et al., "Investigation of the effect of the nature and concentration of binders of the properties of dry–process paper," *Sb. Tr. Tsentr. Nauch.–Issled. Bumagi*, 9:117–123 (1974).

Gugliemelli et al., "Base–Hydrolyzed Starch–Polyacrylonitrile (S–PAN) Graft Copolymer. S–PAN–1:1, Pan M.W. 794,000*", *J. of Applied Copolymer Science*, 13:2007–2017 (1969).

Hoque et al., "Granulation and Tabletting of Iron Oxide–Chromic Oxide Catalyst Mass with the Aid of Binding Ingredients Part II–Cellulosic Derivatives and Polyethylene Glycol as Binding Ingredients,"*Fertilizer Technology*, 20:30–35 (1983).

Linday, "Absorbent Starch Based Co–polymers—Their Characteristics and Applications," *Formed Fabrics Industry*, pp. 20, 24 and 26 (May 1977).

Lysogorskaya et al., "Effect of Moisture Content on the Development of Interfiber Bond in Air–Laid Paper," *Leningrad Technological Institute of the Pulp and Paper Industry*, Zh. Prikl, Khim., 63:(8) 1869–1872 (1990).

Lysogorskaya et al., "Effect of Moisture Content on Development of Interfiber Bonding in the Structure of Air–Dried Paper," *Plenum Publ. Corp*, pp. 1730–1733 (1991).

Ogurtsov et al., "Effect of the modulus of elasticity of the binder on the properties of dry–process paper," *Sb. Tr. Tsentr. Nauch.–Issled. Inst. Bumagi*, 9:123–127 (1974).

S. Lammie, "Use of Glycerine as a Softener for Paper Products," *The World's Paper Trade Review*, pp. 2050, Dec. 13, 1962.

Sliwiok and Kowalska, "Investigation of Self–Association of the Selected Glycols and Cellulose Sorbents," Microchemical Journal, 26:68–74 (Jan. 1992).

"Super slurpers: Time for chang?," *Chemical Week*, pp. 21–22 Jul. 24, 1974.

Weaver et al., "Hydrolyzed Starch–Polyacrylonitrile Graft Copolymers: Effect of Structure on Properties*", *J. of Applied Polymer Science*, 15:3015–3024 (1971).

Weaver et al., "Highly Absorbent Starch–Based Polymer," *Northern Regional Research Laboratory, Agricultural Research Service*, U.S. Dept. of Agriculture, Peoria, Illinois, pp. 169–177.

BINDER TREATED FIBROUS WEBS AND PRODUCTS

CROSS REFERENCE TO RELATED APPLICATIONS

This is a divisional of prior application Ser. No. 08/416,375 filed on Apr. 4, 1995, entitled BINDER TREATED FIBROUS WEBS AND PRODUCTS which now U.S. Pat. No. 5,807,364 is a continuation-in-part application of the following U.S. patent applications, each of which was filed on Aug. 17, 1992, in the names of Michael R. Hansen and Richard H. Young, Sr. Each of these applications is hereby incorporated herein by reference: (1) Ser. No. 07/931,059, entitled "POLYMERIC BINDERS FOR BINDING PARTICLES TO FIBERS" now U.S. Pat. No. 5,543,215; (2) Ser. No. 07/931,277, entitled "NON-POLYMERIC ORGANIC BINDERS FOR BINDING PARTICLES TO FIBERS" now U.S. Pat. No. 5,538,783; (3) Ser. No. 07/931,279, entitled "PARTICLE BINDERS THAT ENHANCE FIBER DENSIFICATION." now U.S. Pat. No. 5,589,256.

This is a divisional of prior application Ser. No. 08/416,375 filed on Apr. 4, 1995, entitled BINDER TREATED FIBROUS WEBS AND PRODUCTS which now U.S. Pat. No. 5,807,364 is also a continuation-in-part of the following U.S. patent applications, each of which was filed on Aug. 17, 1993 in the names of Michael R. Hansen and Richard H. Young, Sr., and each of which is hereby incorporated by reference: (4) Ser. No. 08/107,469, entitled "PARTICLE BINDERS" now U.S. Pat. No. 5,672,418; (5) Ser. No. 08/108,219, entitled "PARTICLE BINDING TO FIBERS" now U.S. Pat. No. 5,607,759; (6) Serial No. 08/107,467, entitled "BINDERS FOR BINDING WATER SOLUBLE PARTICLES TO FIBERS" now U.S. Pat. No. 5,693,411; (7) Ser. No. 08/108,217, entitled "PARTICLE BINDERS" now U.S. Pat. No. 5,547,745; and (8) Ser. No. 08/108,218, entitled "PARTICLE BINDERS TO FIBERS" now U.S. Pat. No. 5,641,561.

This is a divisional of prior application Ser. No. 08/416,375 filed on Apr. 4, 1995, entitled BINDER TREATED FIBROUS WEBS AND PRODUCTS which now U.S. Pat. No. 5,807,364 is also a continuation-in-part of U.S. patent applications (9) Ser. No. 08/197,483, filed Feb. 16, 1994, entitled "DENSIFYING AGENTS FOR ENHANCING FIBER DENSIFICATION" now U.S. Pat. No. 5,547,541; (10) Ser. No. 08/193,301, filed Feb. 7, 1994, entitled "WET LAID FIBER SHEET MANUFACTURING WITH REACTIVATABLE BINDERS FOR BINDING PARTICLES TO FIBERS" now U.S. Pat. No. 5,609,727; (11) Ser. No.08/261,811, filed Jun. 17, 1994, entitled "REACTIVATABLE BINDERS FOR BINDING PARTICLES TO FIBERS" now U.S. Pat. No. 5,571,618; and (12) Ser. No. 08/153,819, filed Nov. 15, 1993, entitled "PARTICLE BINDERS FOR HIGH BULK FIBERS" now U.S. Pat. No. 5,447,977.

The benefit of the filing dates of these earlier applications is hereby claimed under 35 U.S.C. § 120.

FIELD OF THE INVENTION

This invention concerns polymeric and non-polymeric binding agents for fibers and the use of such agents to bind particles to fibers and to enhance the densification of fibers treated with these agents. Treated fibers bind particles and may be easily densified by external application of pressure. The binding agents may be applied to fibers on a wet-laid fiber sheet manufacturing line, and subsequently fiberized for processing using air lay equipment. In particular embodiments, the invention provides densified webs of cellulosic fibers which may then be used, for example, to make densified absorbent fiber cores that are incorporated into liquid absorbent products.

BACKGROUND OF THE INVENTION

Superabsorbent polymers have been developed in recent years that are capable of absorbing many times their own weight of liquid. These polymers, which are also known as water insoluble hydrogels, have been used to increase the absorbency of sanitary products such as diapers and sanitary napkins. Superabsorbent polymers are often provided in the form of particulate powders, granules, or fibers that are distributed throughout absorbent cellulosic products to increase the absorbency of the product. Superabsorbent particles are described, for example, in U.S. Pat. No. 4,160,059; U.S. Pat. No. 4,676,784; U.S. Pat. No. 4,673,402; U.S. Pat. No.5,002,814; and U.S. Pat. No. 5,057,166. Products such as diapers that incorporate absorbent hydrogels are shown in U.S. Pat. No. 3,669,103 and U.S. Pat. No. 3,670,731. Other types of particles, that perform specific desired functions in end products, are also sometimes added to fibrous webs. These particles include, for example, antimicrobials, fire retardants, zeolites, odor absorbents, and the like.

One problem with the use of particles to impart properties to a fibrous web is that the particulate material can be physically dislodged from the fibers of an absorbent product. The physical separation of particles from fibers usually takes place during mechanical handling and transportation of the particle-containing fibrous web. This separation leads to undesirable and deleterious effects on the end product. For example, separation of superabsorbent particles from its substrate usually reduces the absorbency of the product and diminishes the effectiveness of the superabsorbent material. This problem was addressed in European Patent Application 442 185 A1, which discloses use of a polyaluminum chloride binder to bind an absorbent polymer to a fibrous substrate. The polyaluminum binder, however, suffers from the drawback of being an inorganic product that is not readily biodegradable. Moreover, that European patent does not offer any guidance for selecting binders other than polyaluminum chloride that would be useful in binding absorbent particles.

A method of immobilizing superabsorbents is disclosed in U.S. Pat. No. 4,410,571 in which a water swellable absorbent polymer is converted to a non-particulate immobilized confluent layer. Polymer particles are converted to a coated film by plasticizing them in a polyhydroxy organic compound such as glycerol, ethylene glycol, or propylene glycol. The superabsorbent assumes a non-particulate immobilized form that can be foamed onto a substrate. The individual particulate identity of the superabsorbent polymer is lost in this process. The confluent nature of the superabsorbent material can also result in gel blocking, in which absorption is diminished as the water swollen polymers block liquid passage through the film layer.

U.S. Pat. No. 4,412,036 and U.S. Pat. No. 4,467,012 disclose absorbent laminates in which a hydrolyzed starch polyacrylonitrile graft copolymer and glycerol mixture is laminated between two tissue layers. The tissue layers are laminated to each other by applying external heat and pressure. The reaction conditions form covalent bonds between the tissue layers that firmly adhere the tissue layers to one another.

Numerous other patents have described methods of applying binders to fibrous webs. Examples include U.S. Pat. No.

2,757,150; U.S. Pat. No. 4,584,357; and U.S. Pat. No. 4,600,462. Such binders are not described as being useful in binding particulates, such as superabsorbent particles, to fibers.

Yet other patents disclose crosslinking agents such as polycarboxylic acids that form covalent intrafiber bonds within individual cellulose fibers, as in European Patent Application 440 472 A1; European Patent Application 427 317 A2; European Patent Application 427 316 A2; and European Patent Application 429 112 A2. The covalent intrafiber bonds are formed at elevated temperatures and increase the bulk of cellulose fibers treated with the crosslinker by forming intrafiber ester crosslinks. The covalent intrafiber bonds produce a fiber product that when airlaid into a fibrous web yields a web that is more difficult to compress to conventional pulp sheet densities than an untreated sheet. Covalent crosslink bonds may also form between the fibers and particles, and thus occupy functional groups of the fibers that would otherwise be available for absorption, hence absorption efficiency is decreased.

A particular disadvantage, for some applications, of forming covalent ester intrafiber crosslinks is that the resulting crosslinked, stiffened fiber product resists densification. Energy requirements for making densified absorbent products are therefore increased because very high compression pressures must be applied to density the absorbent product.

Some of the foregoing and other problems have been overcome by technology of the parent and related applications which provide more readily densified fibrous webs that are made of fibers with hydrogen bonding functional sites, and binders, less volatile than water, that have a functional group capable of forming a hydrogen bond with the fibers, and another or the same functional group that is also capable of forming a hydrogen bond or a coordinate covalent bond with particles. The binders of the parent and related applications are either polymeric or non-polymeric. The polymeric binders may be selected from the polyglycols [especially poly(propyleneglycol)], a polycarboxylic acid, a polycarboxylate, a poly(lactone) polyol such as diols, a polyamide, a polyamine, a polysulfonic acid, a polysulfonate and the like, and combinations thereof Specific listed examples of some of these binders, are as follows: polyglycols including polypropylene glycol (PPG) and polyethylene glycol (PEG); poly(lactone) diols including poly(caprolactone) diol; polycarboxylic acid including polyacrylic acid (PAA); polyamides including polyacrylamide or polypeptides; polyamines including polyethylenimine and polyvinylpyridine; polysulfonic acids or polysulfonates including poly(sodium4-styrenesulfonate) or poly(2-acrylamido-methyl-1-propanesulfonic acid); and copolymers thereof (for example a polypropylene glycol/polyethylene glycol copolymer).

The non-polymeric binder noted above is disclosed as having a volatility less than water and has at least one functional group that is capable of forming a hydrogen bond or coordinate covalent bond with the particles, and at least one functional group that is capable of forming hydrogen bonds with the cellulose fibers. The non-polymeric binder is described as an organic binder including a functional group selected from a carboxyl (for example, carboxylic acids), a carboxylate, a carbonyl (for example, aldehydes), a sulfonic acid, a sulfonate, a phosphoric acid, a phosphate, a hydroxyl (for example, an alcohol or polyol), an amide, amine, and the like, and combinations thereof (for example, amino acid or hydroxy acid), wherein there are at least two functionalities on the molecule selected from this group, and the two functionalities are the same or different. Polyols, polyamines (a non-polymeric organic binder with more than one amine group), polyamides (a non-polymeric organic binder with more than one amide group), polycarboxylic acids (a non-polymeric organic binder with more than one carboxylic acid functionality), amino alcohols, and hydroxy acids are listed as examples of such binders. These binders have functional groups that are capable of forming the specified bonds with the particles and fibers.

The amount of binder present is described as depending on a number of factors, including the nature of the binder and particles, and whether the particles are immediately added to the fibers or after a period of time. Hence, one skilled in the art will realize that the amount of binder suitable and particularly useful for a particular application will vary. However, it is disclosed that the binder may suitably be present in an amount of from about 1 to 80 percent of the total weight of the fibrous material An especially suitable disclosed range of binder is 1 to 40 percent by weight, or 1 to 25 percent by weight of the fibrous material. The particles bound by the binder (via hydrogen/coordinate covalent bonds) may suitably be present in an amount of 0.05 to 80 percent, preferably 1 to 80 percent or 3 to 80 percent, or more than 3 percent by weight of the total weight of the fibrous material and the particles.

A particularly suitable range of particles disclosed in the related applications is 3 to 40 percent by weight of the fibrous material and particles. A preferred weight ratio of particle to binder is 8:1 to 50:1. Suitable particles are superabsorbent polymer particles such as a starch graft polyacrylate hydrogel fines or larger size particles such as granules, which form hydrogen bonds with the binder. The related applications teach that the binder also forms hydrogen bonds with the hydroxyl groups of the cellulose, thereby securely attaching the superabsorbent particles to the fibers.

In some instances, according to the related applications, the binder is associated with the fibers as a solid (for example, a dry powder or a dried liquid), and the fibers contain at least 7 percent water by weight when the binding step is performed. This level of moisture in the fibers provides sufficient mobility of reactants to allow the particles and fibers to bind well to each other. When a liquid binder is used (for example, glycerin or a solution of glycine powder), the fibers suitably contain at least about 0.05 percent water by weight.

Moreover, it is discussed that the capacity for activation or reactivation allows the binder to be applied to the fibers, which are then shipped to distribution points with the binder in an inactive form. The binder is then activated at the distribution point (for example, a customer's facility) where particles are added to the fibers and bound thereto. As used therein, binder "activation" includes both activation of previously inactive binders (such as solid binders in the absence of liquid) or reactivation of previously active binders (such as a liquid binder that has been dried).

Of the useful binders, a significant proportion are acidic so that the pH of a liquid absorbent product may be adjusted when the product is wetted with, for example, synthetic urine. It is generally preferred, however, for health reasons that the pH of disposable diapers, a commercially important product using particles (especially superabsorbent particles), be maintained at above about pH 4 and as close to a neutral pH as possible.

Despite the availability of binders using a hydrogen bonding and/or coordinate covalent bonding mechanism for binding particles to fibers and fibers to fibers, there exists a need for binders that more strongly attach the particles to the fibers. This need is especially critical when the fiber-particle combination must undergo intensive mechanical handling, as in transportation, storage and reprocessing of the combined material Under such intensive handling, it has been found that particles bound by a binder through hydrogen bonding or coordinate covalent bonds to fibers may become dislodged and migrate from a position where their presence is required.

SUMMARY OF THE INVENTION

The invention provides fibrous webs containing binders that bind particulates to fibers and sometimes, fibers to fibers, and that enhance the densification of the webs. The particle-fiber bond provided is of sufficient strength to withstand the usual handling that a particle-containing fibrous web undergoes during transportation and during reprocessing for use in a finished product. Moreover, the invention provides binder-containing fibrous webs that retain a pH above about 4, when the web is wetted.

More particularly, in one aspect, the binders of the present invention are ionizable salts of organic hydroxy acids, especially acids such as carboxylic acids, phosphoric acids, phosphonic acids, phosphinic acids, sulfonic acids or nonreactive combinations thereof It is theorized, without being bound, that upon ionizing, the ionized acidic moiety forms a "hybrid" ionic bond with functional sites on fibers or particles, such as superabsorbent polymer particles, while the hydroxy group of the hydroxy acid binder forms bonds with functional groups on the other material, such as hydrogen or "hybrid" ionic bonds. As a result, a strong fiber-particle linkage is formed which resists the mechanical forces created by handling, transportation and reprocessing of a particle-containing fibrous web.

Alternatively, the binder may include an ionizable acidic moiety capable of forming a "hybrid" ionic bond with functional groups on the fibers, and a functional group capable of forming a coordinate covalent bond with the particles. Again, as a result, a strong fiber-particle linkage is formed that resists the mechanical forces created by handling, transportation and reprocessing of a particle-containing fibrous web.

As a consequence of using the acid salts of hydroxy acids, the binders of the present invention do not provide as marked a pH decrease as the use of the hydroxy acids themselves as binders. Thus, the pH may be maintained at a level above about 4, and in many instances at a neutral level, so that the binders may be used to form particle-fiber webs that are useful in such products as disposable diapers, incontinence diapers, and like products where it is desired to maintain a pH above about 4.

Moreover, the binders of the present invention may be used together with hydroxy acids, which also act as binders. In this combination, the salts of the hydroxy acids act as buffers, as well as binders, so that the pH may be maintained at a desired level by suitable selection of the relative proportions of acid and salt.

In another aspect, the binders of the present invention are organic salts of a base. Such binders have at least one functional group capable of interacting ionically with functional groups on the fibers or particles, particularly superabsorbent particles or cellulose fibers and at least one functional group capable of forming hydrogen bonds, coordinate covalent bonds, "hybrid" ionic bonds, or ionic bonds with functional groups on the particles or hydrogen bonds, "hybrid" ionic bonds, or ionic bonds with functional groups on the fibers. For example, a suitable binder would include a cationic salt and an anionic species, such as protonated primary, secondary or tertiary amines or deprotonated quarternary ammonium salts. Other types of suitable binders would include two functional groups comprising cationic salts. Examples of such organic salts of a base include choline chloride.

Examples of materials that can act like either the salts of the hydroxy acids or the organic salts of bases to bind particles to fibers in accordance with the present invention include amino acids. The simple amino acids, such as glycine, sarcosine, alanine, and β-alanine, will include a cationic species and a carboxyl group when the pH is low, a cationic species and an anionic carboxylate species when the pH is near neutral, and an unprotonated amine and an anionic species when the pH is high When the cationic species is present, the amino acid will act like the organic salt of a base and form ionic bonds with anionic groups on the fibers or particles. The hydroxyl groups of the carboxyl functionality of the amino acid will then form a hydrogen or "hybrid" ionic bond with the particles when the ionic bond is formed with the fibers or a hydrogen or "hybrid" bond ionic with the fibers when the ionic bond is formed with the particles. When the acid group is deprotonated, the anionic species can form "hybrid" ionic bonds with either the particles or the fibers and the amine group if unprotonated, can form a hydrogen or coordinate covalent bond with the particles when the "hybrid" ionic bond is formed with the fibers or a hydrogen bond with the fibers when a "hybrid" ionic bond is formed with the particles. Alternatively, when the pH is such that the amino functionality is protonated and the carboxyl functionality is deprotonated at the same time, the ammonium functionality can form an ionic bond with the fibers while the carboxylate functionality can form a "hybrid" ionic or ionic bond with the particles or, the ammonium functionality can form an ionic bond with the particles while the carboxylate functionality can form a "hybrid" ionic bond with the fibers. Furthermore, for those amino acids that include two or more amine groups, when at least two of the amine groups is protonated, one of the protonated amine groups can form an ionic bond with an anionic species on the fiber and the other protonated amine group can form an ionic bond with an anionic species on the particles.

In accordance with the present invention, the binders comprising salts of hydroxy acids or organic salts of bases can be used in conjunction with various binding systems described in the background of the invention. For example, a preferred binding system includes sorbitol, glycerin, lactic acid and sodium lactate. In the preferred binding system, sodium lactate is used in an amount ranging from about 0.5 to about 10.0%, lactic acid in an amount ranging from about 0 to about 10.0%, glycerin in an amount of about 0 to about 20.0%, and sorbitol in an amount of about 0 to about 15.0%, based on the total weight of the added material and fiber.

Accordingly, the invention also provides for the use of an optional softener, in the event that the binder itself does not perform the softening function, or in addition to a softening binder, if additional softening is necessary. Thus, softeners such as sorbitol, glycerin, propylene glycol, or butylene glycol may be added to the particle-containing fibrous webs of the invention to provide a softening effect.

Importantly, the particle-containing fibrous webs using the salts of hydroxy acids or organic salts of bases as binders, according to the invention, are more readily densified than fibrous webs not containing the binders. Thus, the fibrous webs of the invention may be densified to densities of from about 0.06 grams per cc. to about 0.7 grams per cc., using an applied pressure of from about 0 psi to about 1000 psi. In general, the densification process does not require the addition of heat and may be carried out by compressing the fibrous particle and binder-containing web between compression rollers.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF SEVERAL PREFERRED EMBODIMENTS OF THE INVENTION

I. Processing of Fibers

Figure 1:
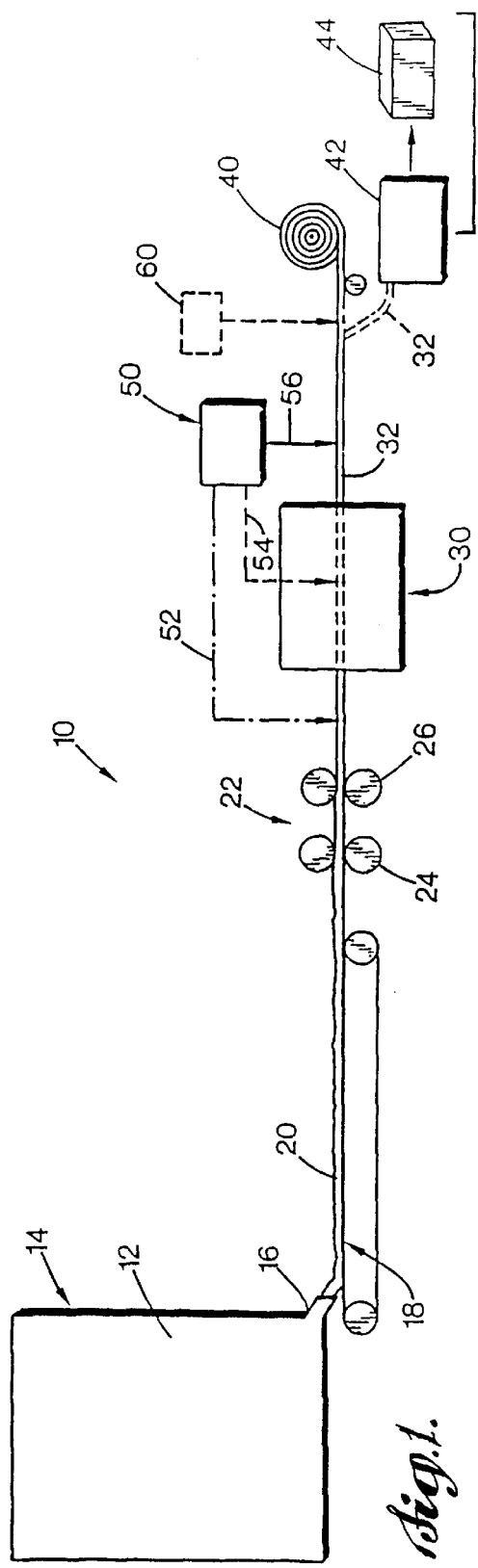
FIG. 1 is a schematic illustration of a wet laid sheet manufacturing line illustrating the application of binders in accordance with the present invention during the manufacture of a fiber sheet.
Figure 2:
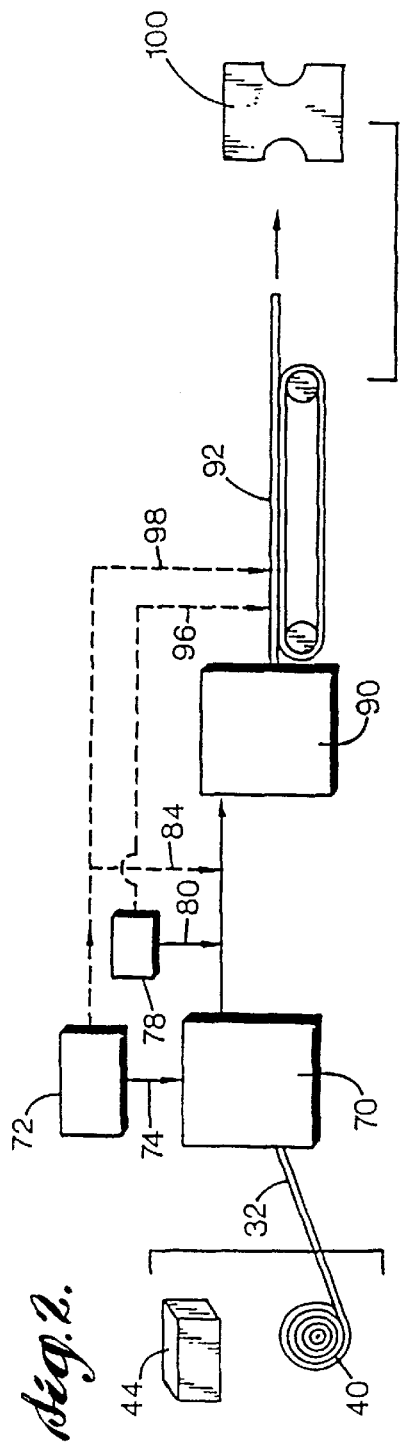
FIG. 2 is a schematic illustration of a binder activation and particle attachment process in accordance with the present invention.

FIG. 1 illustrates a wet laid sheet manufacturing line such as a pulp sheet manufacturing line 10. In this manufacturing line, a pulp slurry 12 is delivered from a headbox 14 through a slice 16 and onto a Fourdrinier wire 18. The pulp slurry 12 typically includes cellulose fibers such as wood pulp fibers and may also include synthetic or other non-cellulose fibers as part of the slurry. Water is drawn from the pulp deposited on wire 18 by a conventional vacuum system, not shown, leaving a deposited pulp sheet 20 which is carried through a dewatering station 22, illustrated in this case as two sets of calendar rolls 24, 26 each defining a respective nip through which the pulp sheet or mat 20 passes.

In a preferred embodiment, from the dewatering station, the pulp sheet 20 enters a drying section 30 of the pulp manufacturing line. In a conventional pulp sheet manufacturing line, drying section 30 may include multiple canister dryers with the pulp mat 20 following a serpentine path around the respective canister dryers and emerging as a dried sheet or mat 32 from the outlet of the drying section 30. Other alternate drying mechanisms, alone or in addition to canister dryers, may be included in the drying stage 30. The dried pulp sheet 32 has a maximum moisture content pursuant to the manufacturer's specifications. Typically, the maximum moisture content is no more than 10% by weight of the fibers and most preferably no more than about 4% to 6% by weight. Otherwise, the fibers tend to be too damp. Unless overly damp fibers are immediately used, these fibers are subject to degradation by, for example, mold or the like. As described below in more detail, binder is preferably applied after the sheet exits the drying stage 40. Typically the binder addition increases the moisture content of the dried sheet 32 to about 6% to 8% by weight. The dried sheet 32 is taken up on a roll 40 for transportation to a remote location, that is, one separate from the pulp sheet manufacturing line, such as at a user's plant for use in manufacturing products. Alternatively, the dried sheet 32 is collected in a baling apparatus 42 from which bales of the pulp 44 are obtained for transport to a remote location. These fibers can be individualized, for example by defiberization in a hammermill.

As described above, a binder, of the type discussed in detail below, is applied to the pulp sheet from one or more binder applying devices, one of which is indicated at 50 in FIG. 1. Any binder applying device may be used, such as sprayers, roll coaters, immersion applicators or the like. Sprayers are typically easier to utilize and incorporate into a pulp sheet manufacturing line. As an alternative to application at arrow 56, as indicated by the arrows 52 and 54, the binder may be applied at various locations or at multiple locations on the pulp sheet manufacturing line, such as ahead of the drying stage 30 (indicated by line 52), or intermediate the drying stage 30 (as indicated by line 54). Water-based binders, such as choline chloride or sodium lactate are preferably applied at a location where their addition will not increase the moisture content of the sheet above the maximum desired moisture content. Consequently, water-based binders are typically applied at location 56. At location 52, the water remaining in the sheet or mat 20 at this stage tends to interfere with the penetration of the water based binder into the sheet. Consequently, application of the water based binder after some drying has taken place, for example at location 54, is preferable over application at location 52. If water-based binders are applied at location 56 in an amount which would cause the moisture content of the sheet to exceed the desired maximum level, an additional drying stage (not shown) may be included in the pulp manufacturing line to bring the moisture content down to the desired level.

When nonaqueous binders such as glycerin, propylene glycol, butylene glycol, or low molecular weight polyethylene glycol are used in combination with the ionizable salts of organic hydroxy acids or organic salts of bases in accordance with the present invention, the various components can be combined and then added downstream from the drying stage at location 56 or during the drying stage as indicated by location 54. Alternatively, liquid non-aqueous binders may be added at a location such as location 52, upstream of the drying stage. At this latter location, the water in the wet web may tend to attract the non-aqueous binders into the mat or sheet as the binders tend to be hydroscopic. Since non-aqueous binders typically do not enhance the degradation of the product due to the addition of moisture to the sheet, they can be applied downstream from the drying stage without bringing the moisture content of the sheet above the desired maximum level.

Preferably, particles are added after defiberization. It is possible to add the particulate materials, selected as explained below, to the sheet and adhered thereto by the binders on the pulp manufacturing line, such as indicated by the particulate applicator 60, which may comprise a bulk or volumetric metering device. These particles may be sprinkled, poured or otherwise added to the sheet. To facilitate the adherence of these particulates to the sheet at this location, enough moisture must remain in the sheet, in the case of aqueous binders, to enable the binding between the particles and fibers as explained below. Particles can be added on the pulp sheet manufacturing line in this manner, with a subsequent drying stage being utilized to reduce the moisture content following particulate addition.

The above approach produces a web wherein the particles are strongly bound to the fibers. This approach also allows the fiber-particle web manufacturer to customize the web for a particular customer's needs. For example, a user may want superabsorbent particles, certain zeolites (e.g., odor absorbing materials which can become saturated with odors over time), or zeolites with silver salts as antimicrobial agents. Therefore, it is possible to now provide a customized fibrous product for the consumer products manufacturer.

When the end user desires to add the particulate material to the fibers itself preferably, the respective rolls 40 or bales 44 of binder-containing fibers, without particles, are transported to a remote location for use by the end user. These rolls or bales (or otherwise transported fibers, e.g., bagged, containerized or otherwise in bulk form) are then refiberized by a fiberizing apparatus 70. Although any fiberizer may be used, a typical fiberizing apparatus 70 is a hammermill which may be used alone or in conjunction with other devices such as picker rolls or the like for breaking up the sheet 32 or bales 42 into individual fibers.

A particulate material adding mechanism 72 (e.g., like mechanism 60) delivers the desired particulate materials to the fibers at the desired location in the end user's process. Again, the device 72 typically comprises a metering mechanism, although any suitable device for adding particulates to fibrous materials may be used. For example, the particulates may be delivered as indicated by line 74 to the fiberizing apparatus 70.

In the case where the salts of organic hydroxy acids or salts of bases are used in conjunction with binders such as those described in the background of the present invention as being previously discovered by the present inventors, agitation of the fibers within the fiberizer 70, may activate certain binders allowing them to contribute to the adherence of the particulates to the fiber through the binder. With respect to activation of the salts of organic hydroxy acids or salts of bases, an activating fluid, which may be a liquid such as water or other liquid that causes disassociation of the counter ions of the binder, particle or fiber, may be sprayed or otherwise applied to the fibers, and optionally the particles, such as from an activation fluid tank or source 78 by way of a sprayer (not shown) at location 80. This activating fluid can serve to activate the binder and facilitate the adherence of the particles to the fibers by the binder.

The particles may then be applied, as indicated by line 84 to the fibers downstream from the application of the activation liquid 80. Alternatively, the particles which may be added prior to or at location 80, are adhered to the fibers by the binder upon activation of the binder at location 80. As yet another alternative, the fiberized fibers are delivered to an air-laying device 90 and reformed into a desired product such as a web indicated at 92. In the case of air-laid fibers, the activation fluid or liquid may be applied to the web at location 96 with the particles then being added at location 98 as shown with the activated binder then adhering the particles to the fibers. The particles may be applied at a location in the process upstream from the application of the activating liquid at location 96. Alternatively, the activating fluid may be added simultaneously with the addition of particles, so that the activation occurs simultaneously with the addition of particles. The activating fluid also may be added after the particles are added to the fibers. In addition, the binder may be activated at specifically defined locations on the web 92, such as in target zones of an absorbent core of a product with the particles then only being applied to these target zones, thereby minimizing the wasting of the particulate material. A specific example of a target zone is the crotch region of a diaper where most diaper wetting would occur. The application of superabsorbent particles to such a zone places these particles at a location where they are most useful in absorbing liquid. The web 92, with or without other components of the end user's product, is then processed into the user's product, such as being included within a disposable diaper 100.

Again, with this approach, the end user of the fibers may readily select particles to be applied to its product and may activate the binder as required to enhance the efficient production of the user's product. In addition, the user has flexibility in air laying or otherwise combining the binder containing fibers into a finished product with the desired particulates. The binder containing fibers, when the binders are all water soluble, are preferably not wet laid because wet laying would remove at least some of the binder.

Not only is handling and shipping of the particulate containing products avoided by the manufacturer of the pulp sheet as described above, enhanced adhesion of particulates to the fibers results because the particles are not subjected to mechanical forces between the location of manufacture of the fibers and the location at which the particulate materials are added.

In accordance with the present invention, absorbent structures or articles may be made from the fibrous web formed in accordance with the present invention. The articles may comprise the fibers of the present invention and adhere particles, such as super absorbent particles. These articles may be composite structures (e.g., made of plural materials). For example, the articles may have the core of plural types of fibers, fiber layers, with or without covering materials. These products are capable of absorbing significant quantities of water and other fluids, such as urine and other body fluids. Such products include, but are not limited to, disposable diapers, sanitary napkins, incontinent pads, towels, bandages, medical wipes, and the like.

Figure 3:
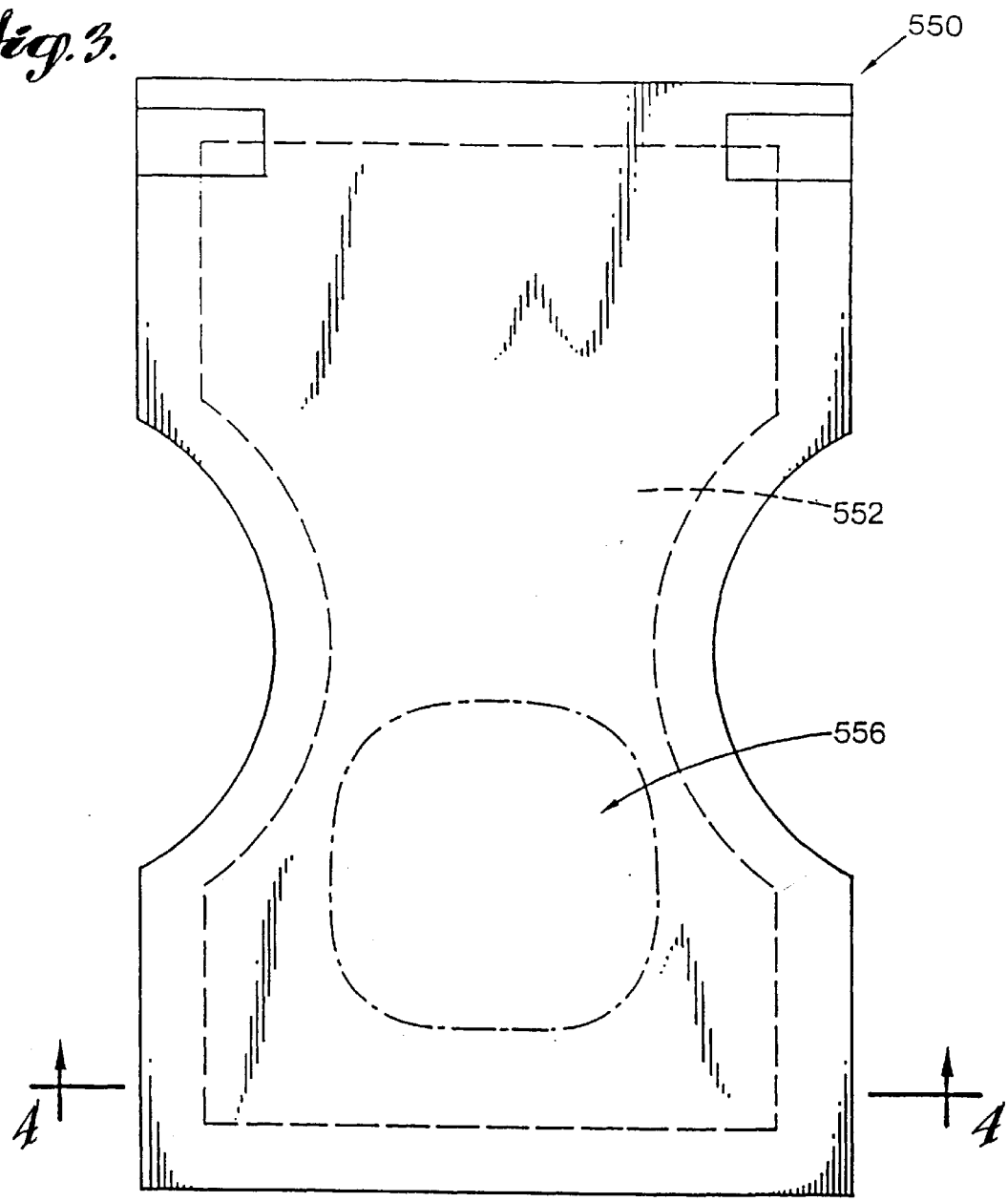
FIG. 3 is a plan view of an absorbent article in the form of a disposable diaper including a web of fibers formed in accordance with the present invention.
Figure 4:
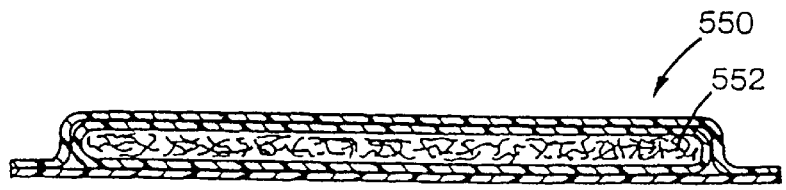
FIG. 4 is a vertical sectional view along line 4—4 of the diaper of FIG. 3.

FIGS. 3 and 4 illustrate a conventional disposable diaper 550 with a core 552 that is comprised of fibers of the present invention with adhered superabsorbent particulate materials. These particulate materials may be confined to a target zone, for example, the front or crotch portion of a diaper indicated at 556 or of a heavier concentration in the target zone.

II. Fiber Characteristics

The present invention includes a method of binding particles to fibers, and the product, including absorbent end-products, that are produced by such method. In particularly preferred embodiments, the product is a cellulosic or synthetic fiber to which superabsorbent hydrogel polymer particles are adhered by a binder, and absorbent products made therefrom. In another particularly preferred embodiment, the product is a fiber to which binders formed in accordance with the present invention have been applied Suitable fibers include wood pulp fibers, which can be obtained from well known chemical processes such as the kraft and sulfite processes. The invention also includes a combination of wood pulp and certain binders, which for the purpose of this combination are bulk fibers in roll form having a basis weight of at least 350 grams per square meter (g/m$^2$) or bale form. The bulk fibers can have a density of at least about 400 kg/m$^3$. Preferred bulk fibers are wood pulp fibers or softwood pulp fibers. Wood pulp fibers can be obtained from mechanical processes, such as ground wood, mechanical, thermomechanical, chemimechanical and chemithermomechanical pulp processes. Also, combinations of these types of fibers can be used. The preferred pulp fiber is chemical, such as kraft fiber. In these processes, the best starting material is prepared from long fiber coniferous wood species, such as pine, spruce and hemlock The fibers are preferably elongated, for example having a length to width ratio of about 10:1 to 5:1.

The fibers useful in the present invention also include fibers that are pretreated prior to the application of a binder to the fibers. This pretreatment may include physical treatment, such as subjecting the fibers to steam or chemical treatment, such as cross-linking the fibers. Although not to be construed as a limitation, examples of pretreating fibers include the application of fire retardants to the fibers, such as by spraying the fibers with fire retardant chemicals. Specific fire-retardant chemicals include, by way of example, sodium borate/boric acid, urea, urea/phosphates, etc. In addition, the fibers may be pretreated with surfactants or other liquids, such as water or solvents, which modify the surface of the fibers. Other pretreatments include exposure to antimicrobials or pigments.

The fibers also may be pretreated in a way which increases their wetability. The fibers also may be pretreated with conventional cross-linking materials and may be twisted or crimped, as desired. Pretreating cellulose fibers with chemicals which result in lignin or cellulose rich fiber surfaces also may be performed in a conventional manner.

Bleaching processes, such as chlorine or ozone/oxygen bleaching may also be used in pretreating the fibers. In addition, the fibers may be pretreated, as by slurrying the fibers in baths containing various solutions. For example, antimicrobial solutions (such as solutions of antimicrobial particles as set forth below), as well as solutions of fertilizers and pesticides, and/or fragrances and flavors, for release over time during the life of the fibers. Fibers pretreated with other chemicals, such as thermoplastic and thermoset resins also may be used. Combinations of pretreatments also may be employed with the resulting pretreated fibers then being subjected to the application of the binder as explained below.

Ground wood fibers, recycled or secondary wood-pulp fibers, and bleached and unbleached wood-pulp fibers can be used. Details of the production of wood pulp fibers are well known to those skilled in the art. These fibers are commercially available from a number of companies, including Weyerhaeuser Company, the assignee of the present invention.

The fibers also can be any of a variety of other natural or synthetic fibers; however, all of the fibers to which binder is applied in accordance with the present invention, and ultimately particles attached, include a functional group having the capability to form a hydrogen bond, "hybrid" ionic bond or an ionic bond with the binder as described below in more detail.

A hydrogen bond is an intermolecular force that occurs between hydrogen atoms that are covalently bonded to small strongly electro-negative elements (such as nitrogen and oxygen) and nonbonding electron pairs on other such electro-negative elements. A hydrogen bonding functionality is a functional group that contains an oxygen or nitrogen atom, for example, hydroxyls, carboxyls, sulfonic acids, phosphoric acids, phosphonic acids, phosphinic acids, sulfonamides, ethers, esters, epoxides, carboxyls, amines, urethanes and others, that is capable of forming a hydrogen bond. The orbital of the nonbonding electron pairs on the oxygen or nitrogen overlap with the relatively empty Is orbital of the hydrogen covalently bonded to another nitrogen or oxygen atom. The Is orbital of the hydrogen is relatively empty due to the unequal sharing of the electrons in the covalent bond between it and the small electro-negative atom (oxygen or nitrogen) to which it is bound. Specific examples of natural fibers that contain hydrogen bonding functionality include silk fibers, wood pulp fibers, bagasse, hemp, jute, rice, wheat, bamboo, corn, sisal, cotton, flax, kenaf, peat moss, and mixtures thereof. Suitable synthetic fibers with hydrogen bonding functionalities include acrylic, polyester, carboxylated polyolefins, rayon, other reconstituted cellulose (tencel) and nylon. The hydrogen bonding functionality is an ester in acrylic fibers and a carboxylic acid in carboxylated polyolefin fibers, an ester in polyester, an amide in nylon, and a hydroxyl in rayon.

A "hybrid" ionic bond in accordance with the present invention may occur between a proton on a carboxyl group and an anion of the binder. The anion competes for the ionizable proton of the carboxyl group. For example, a wood pulp fiber includes a plurality of carboxyl groups. When an ionizable salt of an organic hydroxy acid binder such as sodium lactate in solution is applied to the fibers, the anion of the salt competes for the proton of the carboxyl group. The same type of "hybrid" ionic bonding can occur between the carboxyl groups on superabsorbent materials and the anions of binders in accordance with the present invention. The formation of "hybrid" ionic bonds is favored at lower pHs because the equilibrium disfavors the ionization of the proton on the carboxyl group. On the other hand, at high pHs "hybrid" ionic bonding is not as prominent because the equilibrium favors the ionization of the proton on the carboxyl groups. An illustration of a "hybrid" ionic bond follows:

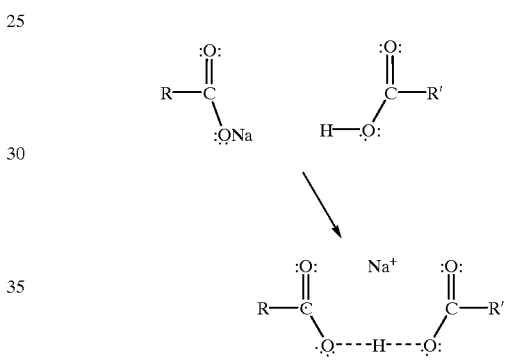

An ionic bond occurs when one or more electrons are transferred from the valence shell of one atom to the valence shell of another. The atom that loses electrons becomes a positive ion or cation while the atom that acquires electrons becomes negatively charged or an anion. The ionic bond results between the attraction between the oppositely charged ions. An example of an ionic bond occurs with the binders that are salts of bases in accordance with the present invention. For example, choline chloride dissociates into the anion chloride and the 2-hydroxyethyl-N, N, N-trimethyl ammonium cation. Choline also includes an hydroxy functionality on the end of the choline molecule opposite the positively charged end. Accordingly, the choline cation can form ionic bonds with ionized carboxyl groups of either the fibers or the particles such as superabsorbent particles. Unlike the "hybrid" ionic bonding, the ionic bonding described above will be favored under conditions that promote the ionization of the carboxyl groups of the fiber or particles. In accordance with the present invention, the hydroxy functional group is available to form hydrogen, "hybrid" ionic, or coordinate covalent bonds with the particles and hydrogen or "hybrid" ionic bonds with the fibers.

For purposes of convenience, and not to be construed as a limitation, the following description proceeds with reference to the treatment of individual chemical wood-pulp fibers. Other types of fibers may also be used in the same process or with variations that will be appreciated by one of ordinary skill in the art.

III. Examples of Useful Particles

In accordance with the present invention, particles are added to the fibers to give the fibers desired properties, such as increased absorbency, abrasiveness, antimicrobial activity or any other desired product characteristic that may be imparted by a particulate additive. Thus, the particle can be any particulate material that has the desired property and that is capable of forming coordinate covalent, "hybrid" ionic, ionic or hydrogen bonds with the binder as described below in more detail.

The prior applications herein incorporated by reference provide detailed descriptions of a multitude of particles that have functional groups capable of forming coordinate covalent bonds and hydrogen bonds. In the previous section, a discussion was provided regarding "hybrid" ionic bonds and ionic bonds. In accordance with the present invention, the types of bonds that the particles are able to form with the binder will depend upon the type of binder employed as well as how the binder interacts with the fibers. For example, if the binder is a salt of an organic hydroxy acid, such as sodium lactate, the particles should be capable of forming either "hybrid" ionic, hydrogen or coordinate covalent bonds with the binder. When the binder interacts with the fibers to form "hybrid" ionic bonds and the binder has free hydrogen bond forming functional groups, the particles should be capable of forming hydrogen bonds with the binder. If the binder interacts with the fibers to form "hybrid" ionic bonds and the binder has free coordinate covalent bond-forming functionality, then the particle should be capable of forming coordinate covalent bonds with the binder. By providing a particle that can form "hybrid" ionic bonds or hydrogen bonds with the binder, one can increase the likelihood of the formation of the "hybrid" ionic bonds because the binder can either form the "hybrid" ionic bond with the fiber or with the particle.

Where the binder is selected from the salts of bases, the particles should be capable of forming coordinate covalent, hydrogen, ionic or "hybrid" ionic bonds with the binder. The ability to form coordinate covalent bonds will be preferred when the binder includes coordinate covalent bond-forming functionality in conjunction with the ionic bond-forming functionality. When the binder includes hydrogen bonding functionality in addition to the ionic bonding functionality, the particles will preferably be capable of forming hydrogen bonds or ionic bonds. In this manner the binder can form hydrogen or ionic bonds with either the fibers or the particles. When the binder includes "hybrid" ionic bond forming functionality in addition to the ionic bond forming functionality, the particles will preferably be capable of forming "hybrid" ionic bonds or ionic bonds. By providing a particle that can form "hybrid" ionic bonds or ionic bonds with the binder, one can increase the likelihood of the formation of the "hybrid" ionic bonds because the binder can either form the "hybrid" ionic bond with the fiber or with the particle.

Particularly preferred particles in accordance with the present invention are superabsorbent particles, which comprise polymers that swell on exposure to water and form a hydrated gel (hydrogel) by absorbing large amounts of water. Superabsorbents are defined herein as material that exhibit the ability to absorb large quantities of liquid, i.e., in excess of 10 to 15 parts of liquid per part thereof. These superabsorbent materials generally fall into three classes, namely starch graft copolymers, crosslinked carboxymethylcellulose derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-crosslinking polyacrylic acid, a crosslinked polyacrylate salt, carboxylated cellulose, and a neutralized crosslinked isobutylene-maleic anhydride copolymer.

These types of superabsorbent particles include functional groups such as carboxyl or carboxylate groups that are capable of forming "hybrid" ionic or hydrogen bonds with the binders in accordance with the present invention or forming ionic bonds with binders formed in accordance with the present invention. As described above, the "hybrid" ionic bonds occur between the proton of the particle carboxyl groups and the anion of the hydroxy acid binder, between the anion of the particle's carboxylate groups and the ionizable proton of a binder carboxyl group, between the anion of the binder's carboxylate groups and the ionizable proton of a fiber carboxyl group, between the anion of the fiber's carboxylate groups and the ionizable proton of a binder carboxyl group. When the salt of a base is used in accordance with the present invention, the superabsorbent particles include neutralized carboxyl groups that upon ionization are available to form ionic bonds with the cation of the basic salt.

Superabsorbent particles are available commercially, for example starch graft polyacrylate hydrogel fines (IM 1000F) from Hoechst-Celanese of Portsmouth, Va., or larger particles such as granules. Other superabsorbent particles are marketed under the trademarks SANWET (supplied by Sanyo Kasei Kogyo Kabushiki Kaisha), SUMIKA GEL (supplied by Sumitomo Kagaku Kabushiki Kaisha and which is emulsion polymerized and spherical as opposed to solution polymerized ground particles), FAVOR (supplied by Stockhausen of Greensboro, N.C.), and NORSOCRYL (supplied by Atochem). The superabsorbent particles come in a variety of sizes and morphologies, for example IM 1000 and IM 1000F. The 1000F is finer and will pass through a 200 mesh screen whereas IM 1000 has some particles that will not pass through a 60 mesh screen. Another type of superabsorbent particle is IM 5600 (agglomerated fines). Superabsorbent particulate hydrophilic polymers also are described in detail in U.S. Pat. No. 4,102,340. That patent discloses hydrocolloid absorbent materials such as cross-linked polyacrylamides.

The amount of particles added to the fibers can vary widely, for example from 0.05 to 80 percent of the total weight of the fibrous material and particles depending upon the nature of the particles. Antimicrobials, such as chlorhexidine or other nonabsorbent particles, are effective in very low amounts, such as 0.05 to 10 percent. Superabsorbent particles are preferably added in an amount of 3–70 percent, especially 20–40 percent by weight of the fibrous material and particles. The particles may be combined to include more than one type of particle, for example superabsorbent and nonsuperabsorbent particles, or two types of superabsorbent particles. When two types of particles are used, the total weight of the particles should not exceed 80 percent of the total weight of the fibrous material and particles.

IV. Non-Polymeric Binder Characteristics

The particles may be bound to the fibers by a non-polymeric ionizable salt of organic hydroxy acids such as carboxylic acids, phosphoric acids, phosphonic acids, phosphinic acids, sulfonic acids or nonreactive combinations thereof. The vapor pressure of the ionizable binder may, for example, be less than 10 mm Hg at 25° C., and more preferably less than 1 mm Hg at 25° C. The non-polymeric ionizable binders comprise non-polymeric binder molecules wherein the molecules have at least one functional group capable of forming hydrogen bonds or "hybrid" ionic bonds with the fibers. When the at least one functional group is capable of forming hydrogen bonds with the fibers, the non-polymeric ionizable binder molecules have at least one other moiety that is capable of forming a "hybrid" ionic bond with the particles as described above. If the non-polymeric ionizable binder molecules have at least one functional group capable of forming "hybrid" ionic bonds with the fibers, then the binder molecules also include at least one moiety that is capable of forming coordinate covalent, "hybrid" ionic, or hydrogen bonds with the particles as described above. In other words, in accordance with the present invention the non-polymeric ionizable binders include molecules that include at least one moiety capable of forming "hybrid" ionic bonds with either the fibers or the particles. In accordance with the present invention, the non-polymeric ionizable binders may include carboxylates, certain forms of amino acids, sulfonates, phosphates, phosphonates and phosphinates, or a salt of an organic hydroxy acid that includes a carboxyl, sulfonic acid, phosphonic acid, phosphoric acid, phosphonic acid, phosphinic acid or sulfonamide functional group.

Hydroxy acids are acids that contain a hydroxyl group, and include hydroxyacetic acid ($CH_2OHCOOH$), lactic, tartaric, ascorbic, citric, salicylic and gluconic acid. Amino acids, useful in accordance with the present invention, include any amino acid, such as sarcosine, glycine, alanine, valine, serine, proline, threonine, cysteine, glutamic acid, lysine, or β-alanine. Preferred amino acids include sarcosine, glycine, β-alanine, proline, and threonine. It should be understood that in addition to the specific amino acids described above, other amino acids that include at least two amino groups, at least two carboxyl groups or additional hydrogen bonding groups, are useful in accordance with the present invention. Sulfonic acids are compounds that contain a sulfonic acid group ($R—SO_3H$) or a sulfonate ($R—SO_3^-$). Phosphoric acids are compounds that contain a phosphoric acid group ($R—PO_4H_2$) or a phosphate ($R—PO_4H^-$). Phosphonic acids are compounds that contain a phosphonic acid group ($R—PO_3H_2$) or a phosphonate ($R—PO_3H^-$). Phosphinic acids are compounds that contain a phosphinic acid group ($R—PO_2HR'_2$) or a phophinate ($R—PO_2R'_2—$).

Salts of amino-sulfonic acids also can be used, if they are ionizable. One example of an amino-sulfonic acid binder suitable for the present invention is taurine, which is 2-aminoethanesulfonic acid.

Although other non-polymeric ionizable salts of hydroxy acids are suitable as binders in accordance with the discussion above, the binder is preferably selected from sodium lactate or other salts of lactic acid, citric acid, ascorbic acid and gluconic acid Another type of non-polymeric binder useful in accordance with the present invention includes salts of bases capable of forming ionic bonds with the fiber and/or with the particle. The organic salts of a base useful in accordance with the present invention will include a cationic salt coupled with a hydrogen, "hybrid" ionic, coordinate covalent, or ionic bonding functionality. For example, common solution forms of amino acids will provide a cationic salt ($R—NH_3^+$) and a hydrogen, "hybrid" ionic, coordinate covalent or ionic bonding carboxyl group. These salts of organic bases comprise non-polymeric binder molecules wherein the molecules have at least one functional group capable of forming ionic bonds with the fibers or particles. If the binder molecule includes a functional group capable of forming an ionic bond with the fiber, then it will also include at least one moiety capable of forming a hydrogen bond, coordinate covalent, "hybrid" ionic or ionic bond with the particles. If the salt of an organic base binder includes a functional group capable of forming an ionic bond with the particles, then it will also include at least one moiety capable forming a hydrogen, "hybrid" ionic, or ionic bond with the fiber. The salts of the organic bases useful in accordance with the present invention include salts of protonated primary, secondary and tertiary amines or deprotonated quarternary ammonium salts such as alkyl trimethyl ammonium compounds. A specific salt of a base useful in accordance with the present invention for binding particles to fibers is choline chloride. Amino acids may also act like salts of bases when the amine group is protonated.

V. Polymeric Binder Characteristics

According to the invention, the particles may be bound to the fibers by a polymeric binder, which may be water soluble, selected from polymeric forms of the binders that are ionizable salts of hydroxy acids or salts of bases as described above, that, upon ionization, produce an ionized moiety able to form an ionic or "hybrid" ionic bond with the particle or fibers as described above.

Although the invention is not limited to polymeric ionizable hydroxy acid salt binders of particular molecular weights, polymeric binders having a molecular weight greater than 400 grams/mole are preferred because they provide attractive physical properties and are easier to apply. Higher molecular weight solids are less volatile as compared to low-molecular-weight polymeric binders. Ionizable polymeric binders with molecular weights less than 4000 grams/mole are especially preferred because they have minimal volatility and are not likely to evaporate from the fibers. Low molecular weight materials typically are more mobile than are the higher-molecular weight materials. Low molecular weight materials can more easily move to the fiber-particle interface, and are more easily absorbed by the fiber where they are less available to bond the particles to the fibers. The higher molecular weight materials are less apt to be absorbed by the fibers, and are less volatile than the low molecular weight materials. As a result, higher molecular weight polymeric ionizable hydroxy acid salt binders, to a greater extent, remain on the surface of the particles where they are more available to bond particles to fibers. In some particular embodiments, polymers with molecular weights between 4000 and 8000 grams/mole have been used. Binders with molecular weights above 8000 may be used, but such exceedingly high molecular weight polymers may decrease binding efficiency because of processing difficulties.

Combinations of the ionizable non-polymeric and polymeric binders described above, as well as with other binders, also may be used, providing that they are non-reactive. That is, providing that the ionizable binders do not react with each other in a manner which prevents the binders from possessing the hydrogen, coordinate covalent, "hybrid" ionic or ionic bonding capability required to be present for binding with fibers and particles in accordance with the present invention.

VI. Process Advantages

The ionizable hydroxy acid salt binders and ionizable salts of bases of the present invention provide certain advantages over non-ionizable binders. For instance, the binders ionize in aqueous solution so that they are readily applied in a solution form to the fibers. Also binding of particles to the fibers can occur without external application of heat. Hence, if desired, particle binding may occur at ambient temperature.

As with the hydrogen bonding and coordinate covalent binders of the related applications, the binders of the present invention have the advantage of being activatable by addition of a fluid, such as a liquid solvent (sometimes referred to herein as a activation liquid, one example of which is water). Hence, a liquid binder (which would include a solution of a solid or liquid binder, or a binder that has a melting point or softening point near room temperature) can be applied to a cellulose mat in the absence of the particles to be bound and the binder allowed to dry, for example until the fiber product reaches an equilibrium moisture content with the moisture in the ambient air. The binders then may be activated to bind the particles in place. Some of the binders (especially the liquid binders) diffuse throughout the fibers to reach an equilibrium distribution of the binder. Alternatively, the binder can be applied as a solid, for example as particles or a powder. At a later stage of processing, water or another activating fluid or liquid may be added to those portions of the mat where particulate binding is desired. The particles then may be added to the mat and adhered to those portions of the mat that have been moistened. Alternatively, the particles may be added to the mat prior to or simultaneously with activation of the binder. Certain binders may be activated by other means, such as heating or agitation as described in the related applications.

In contrast to the binders of the related applications that relied solely on hydrogen bonding or coordinate covalent bonding, the "hybrid" ionic and ionic binders of the present invention provide stronger binder-particle or binder-fiber bonds, e.g., particles more firmly bound or bound to the same degree with less binder, so that particle-containing fiber webs have greater resistance to mechanical handling in the sense of being less prone to dislodging of particles from the fibrous web. The stronger binder-particle bonding results in less loss of particles from the fibrous web and in addition can translate into the use of less binder to achieve satisfactory retention of the particles within the fibrous web.

The binders of the present invention are typically solids at room temperature; however, they may have melting points low enough to allow them to be applied as liquid hot melts of solid binders. Solid binders can be applied to the fibers as a supersaturated solution or the solid binder may be heated, although some may decompose or react with the fiber, above its melting point and applied to the fibers. Upon solidifying or drying the binder is deactivated. Solid binders may be added to fibers in particulate form, for example, by sprinkling binder particles on the fibers, provided they are fixed by the subsequent application of heat or liquid.

The binding reaction of the present invention can occur across a broad range of pH without requiring a catalyst. A suitable pH range without a catalyst is 1–14, but preferred ranges are 3–8 or 6–8 because such neutral pH ranges will produce fibrous products (such as cellulose products) that are less prone to damage by acid hydrolysis.

When water-insoluble particles are used, the moisture content of the fibers during the binding reaction should be 0.5–50%, suitably 5–40%, or preferably 5–20% water weight of the fibers, binder and particle. A moisture content greater than 20%, preferably 30%, or in the range 20–50%, or 30–50%, can be used even though such high moisture contents interfere with intermediate anhydride formation and inhibits formation of covalent bonds in the production of high-bulk crosslinked fibers. When water-soluble particles are used, the moisture content of the fibers during the binding reaction should be 0.5–30%, suitably 5–25%, preferably 12–20%. Particles may be added to the fibers with the particles distributed throughout a fibrous product without being confined to a surface of the product. The particles can be distributed throughout the depth of a fiber product such as a mat or web.

The binder or binders are suitably present in the treated product in an amount of at least 0.5 percent, and no more than 80 percent, by weight of the fibrous material ("percent by weight"). In especially preferred embodiments, the binder is present in an amount of 0.5–80, or more preferably, 0.5 to 40 or 0.5 to 25 percent by weight of the fibrous material. Below about 0.5 percent, when placed on the fiber, an insufficient amount of binder is present to achieve adequate binding. Using excessive amounts of binder can introduce unnecessary expense into the binding process. High percentages of binder can also cause processing problems because the binder material transfers to equipment surfaces. Therefore, it is often preferred to use no more binder than is required to effectively bind the particles and fibers.

The fibrous product of the present invention (with or without intrafiber crosslinking) may further be densified by external application of pressure. The densified product is compact and easily transported. When the particles are superabsorbent particles, the resulting fibrous product has superior properties as compared to nondensified products. The inventors have found that the binders of the present invention produce a product that can be easily densified with or without particles. The fibers are particularly easily densified when at least 5% by weight of the fibers, particles and binder, more preferably 10%, are SAP particles adhered to the fibers.

In accordance with this invention, the binders may be applied to fibers before, subsequent, or simultaneously with addition of the particles. Simultaneous addition can be accomplished by two separate streams of particles and binder that are simultaneously directed at a fibrous substrate, or alternatively merged immediately or some time prior to impacting against the substrate. Without limiting the invention, it appears that the addition of small amounts of moisture to the particles may help bind superabsorbent particles and perhaps other types of particles to the fiber. For example, exposing the particles to air at 45 percent humidity at 68° F. as they are delivered to binder containing fibers has been found to enhance the particle bonding.

Binding may be performed under conditions that favor formation of "hybrid" ionic or ionic bonds, for example, the pH and pKa and amount of water present should be such to allow for disassociation of counter ions, the intimate contact of the fibers, binder and particle such that the needed hydrogen, coordinate covalent, ionic or "hybrid" ionic bonds form.

The following examples illustrate certain embodiments of the invention, and are not limiting of the invention as described above and claimed here below.

EXAMPLES

Example 1

Comparison of "Hybrid" Ionic Binder with Control and Hydrogen Bonding/Coordinate Covalent Bonding Binders Six samples of an oven-dried pulp sheet made of wood pulp fibers, such as NB416 (available from Weyerhaeuser, Tacoma, Wash.) were selected. Each of the samples were treated with a solution of the liquids shown in Table 1, with the exception of the control sheet to which no liquid was added, so that each treated sheet contained 9 weight percent nonvolatile additives and 91 weight percent pulp fibers.

In order to test how effectively superabsorbent polymer particles (SAP) would bind to the liquid treated fibers, each pulp sheet was treated as follows. After liquid treatment, the pulp sheets were allowed to dry overnight. Then, a portion of each treated pulp sheet was selected and fed into a Fitz hammermill fitted with a one-inch square holed screen together with sufficient superabsorbent polymer particles (IM 3900 from Hoechst Celanese, Portsmouth, Va.) to produce a fluff material that contained 40% SAP. The resulting material, a mixture of fiberized sheet and particles, was shunted to an airlay machine and airlaid into a web. Thus, six airlaid webs were prepared: one consisting of the fiberized control sheet and particles, the other five consisting of fiberized liquid treated pulp sheets and superabsorbent particles.

Sections of each of the webs were then subjected to agitation in a column of sieves to separate out any unattached superabsorbent polymeric particles. The particulate loss for each sheet was recorded, and is shown in Table 1 as a percent of the initially added superabsorbent.

The pH of the sheets was determined by immersing a one gram sample of each sheet in 150 milliliters of deionized water and then testing the pH of the solution with a calibrated pH meter.

TABLE 1

Grams of Listed Material Added to Fibers

| Sample | Sorbitol | Glycerin | Lactic acid | Sodium Lactate | % SAP Loss | pH |
|---|---|---|---|---|---|---|
| Control | 0 | 0 | 0 | 0 | 51.64 | 6.2 |
| 1 | 70 | 30 | 0 | 0 | 44.42 | 6.2 |
| 2 | 70 | 30 | 30 | 0 | 1.05 | 3.2 |
| 3 | 70 | 30 | 15 | 0 | 4.32 | 3.4 |
| 4 | 70 | 30 | 9.8 | 25.3 | 5.74 | 4.3 |
| 5 | 70 | 30 | 3.9 | 33.3 | 38.32 | 10.6 |

From the Table 1, it is clear that the loss of superabsorbent polymeric particles was highest from the untreated control sheet. A 70/30 solution of sorbitol/glycerin was not a very effective binder, only retaining about 7% more particles than an untreated sheet. The addition of lactic acid (a hydroxy acid) to the treating liquid dramatically reduced SAP loss to about 1%; however, the pH of the sheet decreased to 3.2, in certain applications an unacceptably low value. Reducing the amount of lactic acid added, to 15 grams, increased SAP loss by a factor of 4, while only marginally increasing pH.

The addition of about 25 grams of sodium lactate, a salt of an organic hydroxy acid, to the liquid mixture containing sorbitol/glycerin and lactic acid, resulted in SAP loss of about 5.7%, while providing a sheet pH above 4.0. Moreover, when sodium lactate was increased to 33 grams, and lactic acid was reduced to about 4 grams, the sheet pH increased to about 11, well above the neutral pH desired. However, at this high pH, and low lactic acid concentration, the SAP loss increased to about 38%.

Example 2

Amino Acid Binders

The following example illustrates how certain amino acids, sarcosine and gluconic acid can be used to produce pulps with varying SAP attachment capabilities Samples of the various acids set forth in Table 2 with appropriate functionality were acquired and 150 gram portions were weighed out. 175 grams of deionized water was added to attempt dissolution. The pH of the solutions were altered by adding either solid NaOH or a 37% solution of HCl as shown in Table 2, until a solution was achieved. Then 500 grams of a 70% sorbitol solution (available from the Arthur Daniels Midland Company, Decatur, Ill., and 155 grams of a 96% glycerin solution available from the Dow Chemical Corporation, Midland, Mich.) were added to each of the acid solutions. The pH of the solutions was determined by dissolving a 1 milliliter aliquot of the acid/sorbitol/glycerin solutions in 9 milliliters of deionized water and checking the pH of that solution with a calibrated pocket pH meter. Samples of NB 416 pulp sheet (available from Weyerhaeuser Company, Tacoma, Wash.) were treated with the mixtures to produce a sheet that was 91% oven dried pulp and 9% nonvolatile additives. The pulp sheet was allowed to air dry overnight. Portions of the treated pulp sheet were fed into a Fitz hammermill fitted with a 1 inch square holed screen while superabsorbent powder (IM 3900 available from Hoeschst Celanese, Portsmouth, Va.) was simultaneously added to the mill in an amount sufficient to produce a fluff material that contained 40% SAP. The resulting material was then shunted to an airlay machine (an M&J airlay machine from M&J Company, Horstens, Denmark) and airlaid into a web. Sections of those webs were each subjected to agitation in a column of sieves in order to separate out unattached SAP. SAP loss for each formulation is set forth in Table 2 below.

TABLE 2

| Sample | initial $H^2O$ | sorbitol | glycerin | neut NaOH | neut HCl | pH | % SAP Loss |
|---|---|---|---|---|---|---|---|
| Arginine | 175 | 500 | 155 | 0 | 55 | 8.51 | 8.45 |
| Aspartic | 175 | 500 | 155 | 45 | 0 | 5.71 | 8.92 |
| Glycine | 175 | 500 | 155 | 65 | 0 | 10.29 | 3.16 |
| Lysine | 175 | 500 | 155 | 40 | 0 | 10.28 | 6.01 |
| β-Alanine | 175 | 500 | 155 | 15 | 0 | 9.74 | 1.96 |
| Gluconic Acid | 175 | 500 | 155 | 0 | 0 | 2.44 | 35.47 |
| Sarcosine | 175 | 500 | 155 | 0 | 0 | 7.13 | 2.14 |
| Glutamic Acid (Base) | 175 | 500 | 155 | 41 | 0 | 5.71 | 12.01 |
| Glutamic Acid (Acid) | 175 | 500 | 155 | 0 | 80 | 1.54 | 7.05 |
| Control | 0 | 500 | 155 | 0 | 0 | 4.1 | 0.91 |
| NB 416 | 0 | 0 | 0 | 0 | 0 | 0 | 39.1 |

The example clearly shows that some of the tested acids effectively attach SAP to the pulp fibers while maintaining a pH above 4.0. The glutanic acid was used in both an acid neutralized and in base neutralized form.

Example 3

Evaluation of Densification Properties of Treated Versus Untreated Fibers

Five samples of an oven-dried pulp sheet made of wood pulp fibers, such as NB416 (available from Weyerhaeuser, Tacoma, Wash.) were selected. Each of the samples were treated with a solution of the liquids shown in Table 1, with the exception of the control sheet to which no liquid was added, so that each treated sheet contained 9 weight percent nonvolatile additives and 91 weight percent pulp fibers.

In order to test how effectively the densification of airlaid webs of the fibers might be effected, each pulp sheet was treated as follows. After liquid treatment, the pulp sheets were allowed to dry overnight. Then, a portion of each treated pulp sheet was selected and fed into a Kamas hammermill. The resulting material was airlaid into pads of 6 inch circles in a laboratory padformer. The pads were then subjected to varying pressures in a press, after which their thicknesses were measured and resultant densities were calculated. Results are shown in Table 3.

TABLE 3

| Sample | Sorbitol | Choline Chloride | Glycerin | Lactic acid | Sodium Lactate | Density 100/125/150 Ψ |
|---|---|---|---|---|---|---|
| Control | 0 | 0 | 0 | 0 | 0 | .086/.097/.103 |
| 1 | 70 | 0 | 30 | 0 | 0 | .110/.115/.125 |
| 2 | 70 | 0 | 30 | 11.15 | 42.1 | .105/.110/.120 |
| 3 | 0 | 70 | 30 | 0 | 0 | .133/.145/.163 |
| 4 | 0 | 70 | 0 | 11.15 | 42.1 | .127/.140/.167 |

From the Table 3, it is clear that the untreated control sheet was less densifiable than the others. Addition of the lactic acid/sodium lactate to the sorbitol/glycerin formulation did not significantly affect the densifiability of fibers treated with those formulations. Replacing the sorbitol with choline chloride significantly improved the densifiability of the treated fibers.

Example 4

Comparison of a Salt of an Organic Base Binder With Control and Hydrogen Bonding/Coordinate Covalent Bonding Binders Five samples of an oven-dried pulp sheet made of wood pulp fibers, such as NB 416 (available from Weyerhaeuser, Tacoma, Wash.) were selected. Each of the samples were treated with a solution of the liquids shown in Table 1, with the exception of the control sheet to which no liquid was added, so that each treated sheet contained 9 weight percent nonvolatile additives and 91 weight percent pulp fibers.

In order to test how effectively superabsorbent polymer particles (SAP) would bind to the liquid treated fibers, each pulp sheet was treated as follows. After liquid treatment, the pulp sheets were allowed to dry overnight. Then, a portion of each treated pulp sheet was selected and fed into a Fitz hammermill fitted with a one-inch square holed screen together with sufficient superabsorbent polymer particles (IM 3900 from Hoechst Celanese, Portsmouth, Va.) to produce a fluff material that contained 40% SAP. The resulting material, a mixture of fiberized sheet and particles, was shunted to an airlay machine and airlaid into a web. Thus, five airlaid webs were prepared: one consisting of the fiberized control sheet and particles, the other four consisting of fiberized liquid treated pulp sheets and superabsorbent particles.

Sections of each of the webs were then subjected to agitation in a column of sieves to separate out any unattached superabsorbent polymeric particles. The particulate loss for each sheet was recorded, and is shown in Table 4 as a percent of the initially added superabsorbent.

TABLE 4

| | Grams of Listed Material Added to Fibers | | | | | |
|---|---|---|---|---|---|---|
| Sample | Sorbitol | Choline Chloride | Glycerin or Propylene Glycol | Lactic acid | Sodium Lactate | % SAP Loss |
| Control | 0 | 0 | 0 | 0 | 0 | 88.60 |
| 1 | 70 | 0 | 30 (G) | 11.15 | 42.1 | 4.10 |
| 2 | 70 | 0 | 30 (PG) | 11.15 | 42.1 | 10.80 |
| 3 | 0 | 70 | 30 (PG) | 30 | 0 | 3.90 |
| 4 | 0 | 70 | 0 | 30 | 0 | 0.60 |

From the Table 4, it is clear that the loss of superabsorbent polymeric particles was highest from the untreated control sheet. Replacing the glycerin with propylene glycol in the sorbitol based formulations adversely affected SAP attachment. However binding was markedly improved when sorbitol was replaced with choline chloride and improved even further upon removal of the propylene glycol.

Preferred embodiments of the invention have been described and a person of ordinary sill in the art will appreciate various changes that can be made that are within the spirit and scope of the invention, as described above and as claimed herebelow.

I claim:

1. A method for preparing an absorbent fibrous component of a liquid absorbent products the method comprising:
   (a) selecting fibers from the group consisting of natural and synthetic fibers; and
   (b) forming a non-woven fibrous mass by adding a binder to the fibers, the binder comprising a salt of an organic hydroxy acid for attaching particles to the fibers, the binder including at least one functional group capable of forming a hybrid ionic bond with the fibers or the particles and another functional group capable of forming a bond with the fibers when the binder forms a hybrid ionic bond with the particles or a bond with the particles when the binder forms a hybrid ionic bond with the fibers.

2. The method of claim 1, wherein the bond with the fibers when the binder forms a hybrid ionic bond with the particles is a hydrogen or hybrid ionic bond and the bond with the particles when the binder forms a hybrid ionic bond with the fibers is a hydrogen, a coordinate covalent, or hybrid ionic bond.

3. The method of claim 1, wherein the organic hydroxy acid is selected from the group consisting of carboxylic acids, phosphoric acids, phosphonic acids, phosphinic acids, sulfonic acids, and nonreactive combinations thereof.

4. The method of claim 3, wherein the organic hydroxy acid is lactic acid.

5. The method of claim 3, wherein the salt of an organic hydroxy acid is sodium lactate.

6. The method of claim 1, further comprising the step of compressing the fibrous mass under sufficient pressure to increase the density of the mass.

7. The method of claim 6, further comprising the step of adding superabsorbent particles to the fibrous mass prior to the densification step.

8. The method of claim 7, further comprising the steps of adding glycerin, sorbitol and lactic acid to the fibrous mass prior to the densification step.

9. The method of claim 1, further comprising the step of adding a fiber softener to the fibrous mass.

10. A method for preparing an absorbent fibrous component of a liquid absorbent product, the method comprising:

(a) selecting fibers from the group consisting of natural and synthetic fibers; and (b) forming a non-woven fibrous mass by adding a binder to the fibers, the binder comprising a salt of an organic base for attaching particles to the fibers, the binder including at least one functional group capable of forming an ionic bond with the fibers or the particles and another functional group capable of forming a hydrogen, hybrid ionic, or ionic bond with the fibers when the binder forms an ionic bond with the particles or a hydrogen, coordinate covalent, hybrid ionic or ionic bond with the particles when the binder forms an ionic bond with the fibers.

11. The method of claim 10, wherein the organic base is selected from the group consisting of protonated primary, secondary and tertiary amines and deprotonated quarternary ammonium salts.

12. The method of claim 10, further comprising the step of compressing the fibrous mass under sufficient pressure to increase the density of the mass.

13. The method of claim 12, further comprising the step of adding superabsorbent particles to the fibrous mass prior to the densification step.

14. The method of claim 10, further comprising the step of adding a fiber softener to the fibrous mass.

15. A method for preparing an absorbent fibrous component of a liquid absorbent product the method comprising:

(a) selecting fibers from the group consisting of natural and synthetic fibers; and (b) forming a non-woven fibrous mass by adding a binder to the fibers, the binder comprising an amino acid for attaching particles to the fibers, the binder including at least one functional group capable of forming a hybrid ionic or ionic bond with the fibers or the particles and another functional group capable of forming a bond with the fibers when the binder forms a hybrid ionic or ionic bond with the particles or a bond with the particles when the binder forms a hybrid ionic bond with the fibers.

16. The method of claim 15, wherein the bond with the fibers when the binder forms a hybrid ionic or ionic bond with the particles is a hydrogen, hybrid ionic or ionic bond and the bond with the particles when the binder forms a hybrid ionic or ionic bond with the fibers is a hydrogen, hybrid ionic, ionic or coordinate covalent bond.

17. The method of claim 15, wherein the amino acid is selected from the group consisting of sarcosine, glycine, alanine, valine, serine, proline, threonine, cysteine, glutamic acid, lysine, or β-alanine.

18. The method claim 17, wherein the amino acid is selected from the group consisting of sarcosine, glycine, β-alanine, proline and threonine.

19. The method of claim 15, further comprising the step of compressing the fibrous mass under sufficient pressure to increase the density of the mass.

20. The method of claim 19, further comprising the step of adding a superabsorbent polymeric particle to the fibrous mass prior to the densification step.

21. The method of claim 15, further comprising the step of adding a fiber softener to the fibrous mat prior to the densification step.

22. The method of claim 4, further comprising the step of adding glycerin, sorbitol, lactic acid, or propylene glycol to the fibers.

23. A The method of claim 7, wherein the superabsorbent particles are added to the fibers in an amount ranging from about 0.05 to 80% of the total weight of the fibers and particles.

24. The method of claim 13, wherein the superabsorbent particles are added to the fibers in an amount ranging from about 0.05 to 80% of the total weight of the fibers and particles.

25. The method of claim 20, wherein the superabsorbent particles are added to fibers in an amount ranging from about 0.05 to 8.0% of the total weight of the fibers and particles.

26. The method of claim 4, further comprising the step of adding propylene glycol and lactic acid.

27. The method of claim 4, further comprising the step of adding sorbitol, propylene glycol and lactic acid to the fibers.

28. A method for preparing a fibrous mass for attachment to particles, the method comprising:

(a) selecting fibers from the group consisting of natural and synthetic fibers; and (b) forming a fibrous mass by adding a binder to the fibers, the binder comprising choline chloride for attaching particles to the fibers.

* * * * *

UNITED STATES PATENT AND TRADEMARK OFFICE
CERTIFICATE OF CORRECTION

PATENT NO. : 6,071,549
DATED : June 6, 2000
INVENTOR(S) : M.R. Hansen

It is certified that error appears in the above-identified patent and that said Letters Patent is hereby corrected as shown below:

| COLUMN | LINE | ERROR |
|---|---|---|
| 24 (Claim 25, | 41 line 3) | "8.0%" should read --80%-- |

Signed and Sealed this

First Day of May, 2001

Attest:

NICHOLAS P. GODICI

Attesting Officer    Acting Director of the United States Patent and Trademark Office